United States Patent
Shapovalov et al.

(10) Patent No.: US 6,867,389 B2
(45) Date of Patent: Mar. 15, 2005

(54) LASER CUTTING OF STENTS AND OTHER MEDICAL DEVICES

(75) Inventors: Vitaly Shapovalov, New Hope, MN (US); Vladimir A. Roussov, St. Petersburg (RU); Vadim P. Veiko, St. Petersburg (RU)

(73) Assignee: Scimed Life Systems, Inc., Maple Grove, MN (US)

( * ) Notice: Subject to any disclaimer, the term of this patent is extended or adjusted under 35 U.S.C. 154(b) by 90 days.

(21) Appl. No.: 10/436,873

(22) Filed: May 12, 2003

(65) Prior Publication Data
US 2003/0226833 A1 Dec. 11, 2003

Related U.S. Application Data

(63) Continuation-in-part of application No. 09/681,192, filed on Feb. 15, 2001, now Pat. No. 6,563,080.

(51) Int. Cl.[7] .............................................. B23K 26/00
(52) U.S. Cl. ............................. 219/121.72; 219/121.68
(58) Field of Search ........................ 219/121.72, 121.68, 219/121.69, 121.85

(56) References Cited

U.S. PATENT DOCUMENTS

| | | | |
|---|---|---|---|
| 4,507,789 A | 3/1985 | Daly et al. ..................... 372/92 |
| 4,539,685 A | 9/1985 | Hart et al. ..................... 372/25 |
| 4,827,207 A | 5/1989 | Chieli ........................ 323/316 |
| 5,073,694 A | 12/1991 | Tessier et al. ............ 219/121.7 |
| 5,151,909 A | 9/1992 | Davenport et al. ............ 372/22 |
| 5,243,615 A | 9/1993 | Ortiz et al. .................... 372/34 |
| 5,254,951 A | 10/1993 | Goto et al. ................. 324/426 |
| 5,345,057 A | 9/1994 | Muller ........................ 219/48 |
| 5,378,998 A | 1/1995 | Davies ....................... 330/288 |
| 5,384,798 A | 1/1995 | Zucker et al. ................ 372/26 |
| 5,394,415 A | 2/1995 | Zucker et al. ................ 372/26 |
| 5,421,955 A | 6/1995 | Lau et al. ..................... 216/48 |
| 5,500,503 A | 3/1996 | Pernicka et al. ........ 219/121.64 |
| 5,515,001 A | 5/1996 | Vranish ....................... 330/69 |
| 5,528,611 A | 6/1996 | Scheps ........................ 372/14 |
| 5,530,711 A | 6/1996 | Scheps ........................ 672/20 |
| 5,548,234 A | 8/1996 | Turi et al. .................... 372/14 |
| 5,701,319 A | 12/1997 | Fermann ...................... 372/18 |
| 5,703,340 A | 12/1997 | Ohta et al. ............. 219/121.48 |
| 5,759,192 A | 6/1998 | Saunders .................... 606/194 |
| 5,772,864 A | 6/1998 | Moller et al. ................. 205/73 |
| 5,780,807 A * | 7/1998 | Saunders ............... 219/121.71 |
| 5,788,558 A | 8/1998 | Klein ......................... 451/36 |
| 5,845,275 A | 12/1998 | Le Van Suu ................... 706/1 |
| 5,852,277 A | 12/1998 | Gustafson ............. 219/121.67 |
| 5,902,499 A | 5/1999 | Richerzhagen ......... 219/121.84 |
| 5,906,759 A | 5/1999 | Richter .................. 219/121.63 |

(List continued on next page.)

FOREIGN PATENT DOCUMENTS

| | | |
|---|---|---|
| EP | 0 842 729 A1 | 5/1998 |
| EP | 0 909 553 | 4/1999 |
| WO | 89/03274 | 4/1989 |
| WO | 96/26689 | 9/1996 |
| WO | 99/56907 | 11/1999 |

Primary Examiner—M. Alexandra Elve

(57) ABSTRACT

A desired pattern may be cut into a stent preform by impinging a laser beam onto the stent preform. The laser beam is formed using a laser system comprising a resonator cavity for resonating laser radiation, a gain medium contained in the resonator cavity, a pump for periodically pumping the gain medium and an electro-optical modulator in communication with the resonator cavity. The laser system produces a radiation pulse for each pump period. Each radiation pulse is conditioned by suppressing at least a portion of the pulse. The pulse may also be modulated with an electro-optical modulator to produce a pulse train of ordered pulses of radiation. Each pulse train is output from the optical cavity as an output laser beam which is directed at the stent preform to cut a desired pattern in the stent preform.

23 Claims, 7 Drawing Sheets

U.S. PATENT DOCUMENTS

| | | |
|---|---|---|
| 5,922,005 A | 7/1999 | Richter et al. .............. 606/192 |
| 5,951,881 A | 9/1999 | Rogers et al. ................ 216/41 |
| 5,972,018 A | 10/1999 | Israel et al. ................. 606/198 |
| 5,994,667 A | 11/1999 | Merdan et al. ........ 219/121.67 |
| 6,011,413 A | 1/2000 | Hayakawa et al. ........... 327/51 |
| 6,053,940 A | 4/2000 | Wijay ............................ 623/1 |
| 6,118,293 A | 9/2000 | Manhaeve et al. .......... 324/765 |
| 6,160,240 A * | 12/2000 | Momma et al. ....... 219/121.85 |
| 6,160,441 A | 12/2000 | Stratakos et al. ........... 327/540 |
| 6,407,532 B1 | 6/2002 | Ruha ......................... 320/128 |

\* cited by examiner

LASER CUTTING OF STENTS AND OTHER MEDICAL DEVICES

This application is a continuation-in-part of U.S. application Ser. No. 09/681,192 filed Feb. 15, 2001 now U.S. Pat. No. 6,563,086, the contents of which is incorporated herein in its entirety by reference.

BACKGROUND OF THE INVENTION

A stent is a radially expandable endoprosthesis which is adapted to be implanted in a body lumen. Stents are typically used in the treatment of atherosclerotic stenosis in blood vessels and the like to reinforce body vessels and to prevent restenosis following angioplasty in the vascular system. They have also been implanted in urinary tracts and bile ducts and other bodily lumen. They may be self-expanding or expanded by an internal radial force, such as when mounted on a balloon.

Delivery and implantation of a stent is accomplished by disposing the stent about a distal portion of the catheter, percutaneously inserting the distal portion of the catheter in a bodily vessel, advancing the catheter in the bodily lumen to a desired location, expanding the stent and removing the catheter from the lumen. In the case of a balloon expandable stent, the stent is mounted about a balloon disposed on the catheter and expanded by inflating the balloon. The balloon may then be deflated and the catheter withdrawn. In the case of a self-expanding stent, the stent may be held in place on the catheter via a retractable sheath. When the stent is in a desired bodily location, the sheath may be withdrawn allowing the stent to self-expand.

In the past, stents have been generally tubular but have been composed of many configurations and have been made of many materials, including metals and plastic. Ordinary metals such as stainless steel have been used as have shape memory metals such as Nitinol and the like. Stents have also been made of biodegradable plastic materials. Stents have been formed from wire, tube stock, etc. Stents have also been made from sheets of material which are rolled.

A number of techniques have been suggested for the fabrication of stents from sheets and tubes. One such technique involves laser cutting a pattern into a sheet of material and rolling the sheet into a tube or directly laser cutting the desired pattern into a tube. Other techniques involve cutting a desired pattern into a sheet or a tube via chemical etching or electrical discharge machining.

Laser cutting of stents has been described in a number of publications including U.S. Pat. No. 5,780,807 to Saunders, U.S. Pat. No. 5,922,005 to Richter and U.S. Pat. No. 5,906,759 to Richter.

Most solid state lasers used for cutting purposes work in a free running regime. The typical temporal shape of a laser pulse is shown in FIG. 1. The laser pulse may be characterized as having three main parts. The most intense part of the pulse, labeled as B in FIG. 1, causes fast heating of a metal or other material within the laser beam, melting, splashing or evaporating the material which is useful for cutting. The initial part of the pulse, labeled as A and the tail end of the pulse, labeled as C, produce heating and melting of materials such as metals causing recrystallization of the metal and microcracks and is not as effective in cutting as the more intense portion of the beam. In order to reduce the formation of microcracks, it is desirable to condition the laser beam to transform the less intense portions of the beam into intense spikes of laser radiation.

All US patents and applications and all other published documents mentioned anywhere in this application are incorporated herein by reference in their entirety.

Without limiting the scope of the invention a brief summary of the claimed embodiments of the invention is set forth below in accordance with 37 C.F.R. 1.73. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF INVENTION

The present invention in one embodiment is directed to a method of processing a stent preform comprising the steps of providing a stent preform and a laser system which outputs a laser beam, directing the laser beam at the stent preform and impinging the laser beam onto the stent preform to cut a desired pattern in the stent preform. The laser system used in accordance with the inventive method comprises a resonator cavity for resonating laser radiation, a gain medium contained in the resonator cavity and a pump for periodically pumping the gain medium. A radiation pulse is produced for each pump period. Each radiation pulse is conditioned to produce a pulse train of ordered pulses of radiation with each pulse train being output from the resonator cavity as an output laser beam.

In another embodiment, the invention is directed to a method of processing a stent preform comprising the steps of providing a stent preform and a laser system which outputs a laser beam, directing the laser beam at the stent preform and impinging the laser beam onto the stent preform to cut a desired pattern in the stent preform. The laser system used in accordance with the inventive method comprises an optical cavity for resonating laser radiation, a gain medium contained in the optical cavity and a pump for periodically pumping the gain medium. A radiation pulse is produced for each pump period. Each radiation pulse is conditioned to produce a pulse train of ordered pulses of radiation with each pulse train being output from the optical cavity as an output laser beam.

In another embodiment, the invention is directed to a method of manufacturing a stent comprising the steps of providing a stent preform in the form of a tube or a sheet and providing a laser system comprising an optical cavity for resonating laser radiation, an optical gain medium contained in the optical cavity and an optical pump for periodically pumping the optical gain medium. The laser system produces a radiation pulse for each pump period. The method further comprises the step of conditioning each radiation pulse to produce a pulse train of ordered pulses of radiation which are directed at the stent preform and impinged onto the stent preform to cut a desired pattern in the stent preform. Where the preform is a sheet, the sheet is then formed into a tube.

In another embodiment, the invention is directed to a method of treating a stent comprising the steps of providing a stent, providing a laser system comprising an optical cavity for resonating laser radiation, an optical gain medium contained in the optical cavity and an optical pump for periodically pumping the optical gain medium. The laser system produces a radiation pulse for each pump period. The method further comprises the step of conditioning each radiation pulse to produce a pulse train of ordered pulses of radiation. Each of the pulse trains is directed at desired portions of the stent and impinged onto desired portions of the stent. The pulse trains may be characterized by an amplitude, a pulse width, an inner train separation time between subsequent pulses in a pulse train, and an inter train separation time between subsequent pulse trains. In certain embodiments, the pulses may be conditioned using an electro-optical modulator which forms a part of feedback loop. The amplitude, pulse width, inner train separation time and inter train separation time are selected to polish, harden or engrave those portions of the stent impinged by the pulse trains.

In another embodiment, the invention is directed to a method of treating a workpiece comprising the steps of providing a workpiece and providing a laser system comprising an optical cavity for resonating laser radiation, an optical gain medium contained in the optical cavity and an optical pump for periodically pumping the optical gain medium. The laser system produces a radiation pulse for each pump period. Each radiation pulse is conditioned to produce a pulse train of ordered pulses of radiation, directed at desired portions of the workpiece and impinged onto desired portions of the workpiece. In certain embodiments, the pulses may be conditioned using an electro-optical modulator which forms a part of a feedback loop and the pulse trains may be characterized by an amplitude, a pulse width, an inner train separation time between subsequent pulses in a pulse train, and an inter train separation time between subsequent pulse trains. The amplitude, pulse width, inner train separation time and inter train separation time are selected to perform a treatment selected from the group consisting of engraving, hardening, cutting and polishing.

The invention is also directed to an image processing head for use with a laser. The head comprises a housing having a first opening therein for an input laser beam and a second opening therein for an output laser beam, a first mirror located within the housing, a second mirror located within the housing, a third mirror located within the housing and an optical path extender located within the housing. The first mirror redirects the input laser beam into the optical path extender. The second mirror redirects the laser beam from the optical path extender to the third mirror and the third mirror redirects the laser beam through the second opening in the housing.

The invention is also directed to a method of processing a stent preform comprising the steps of providing a stent preform, providing a laser system which produces a radiation pulse for each pump period. The laser system comprises a) a resonator cavity for resonating laser radiation b) a gain medium contained in the resonator cavity and c) a pump for periodically pumping the gain medium. The method further comprises the steps of conditioning the radiation pulse by suppressing a portion of, but not the entirety of the radiation pulse to produce conditioned radiation, outputting the conditioned radiation in the form of a laser beam, directing the laser beam at the stent preform and impinging the laser beam onto the stent preform to cut a desired pattern in the stent preform.

The invention is also directed to a method of processing a medical device preform comprising the steps of providing a medical device preform, providing a laser system comprising a resonator cavity for resonating laser radiation, a gain medium contained in the resonator cavity and a pump for periodically pumping the gain medium where the laser system producing a radiation pulse for each pump period, conditioning the radiation pulse by suppressing a portion of, but not the entirety of the radiation pulse to produce conditioned radiation, outputting the conditioned radiation in the form of a laser beam, directing the laser beam at the medical device preform, and impinging the laser beam onto the medical device preform to modify the surface of the medical device preform.

Additional details and/or embodiments of the invention are discussed below.

DETAILED DESCRIPTION

Figure 1:
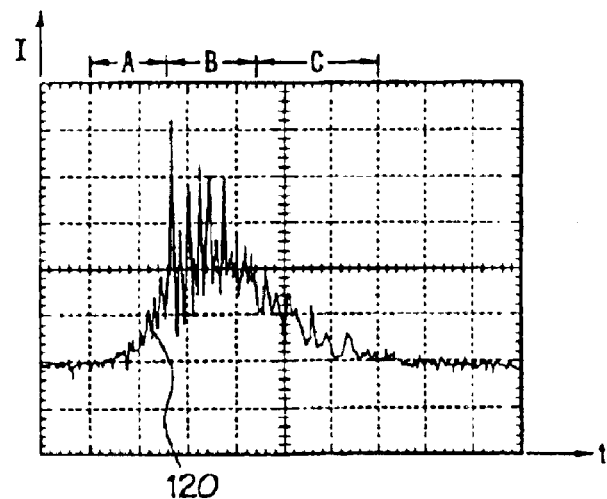
FIG. 1 depicts free lasing radiation as a function of time.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, like reference numerals in the figures shall refer to like features unless otherwise indicated.

The present invention, in some of its embodiments, provides methods for manipulating laser beams for cutting stent preforms, stents and other workpieces. The invention also provides for laser systems for generating the laser beams used in the practice of the inventive methods.

In one embodiment, the present invention is directed to a method of processing a stent preform using a laser beam. The stent preform may be in the form of a tube, a sheet or any other shape of material into which a stent design is cut. Desirably, the stent preform will be made of metal. Typical metals include stainless steel and Nitinol. Other suitable materials for the stent preform include polymeric material, as are known in the art.

The laser system used in accordance with the inventive method comprises a resonator cavity for resonating laser radiation, a gain medium contained in the resonator cavity and a pump for periodically pumping the gain medium. The gain medium is periodically pumped and a radiation pulse is produced for each pump period. Each radiation pulse is conditioned to produce a pulse train of ordered pulses of radiation with each pulse train being output from the resonator cavity as an output laser beam. The laser beam is directed towards the stent preform and impinged onto the stent preform to cut a desired pattern into the stent preform. The laser beam may be moved relative to the stent preform or the stent preform may be moved relative to the laser beam.

Where the preform is in the form of a sheet, once the desired pattern has been cut into the preform, the preform may be rolled into tubular form. Desirably, the edges of the tube may be joined together via welding, the use of adhesives or otherwise.

Figure 2:
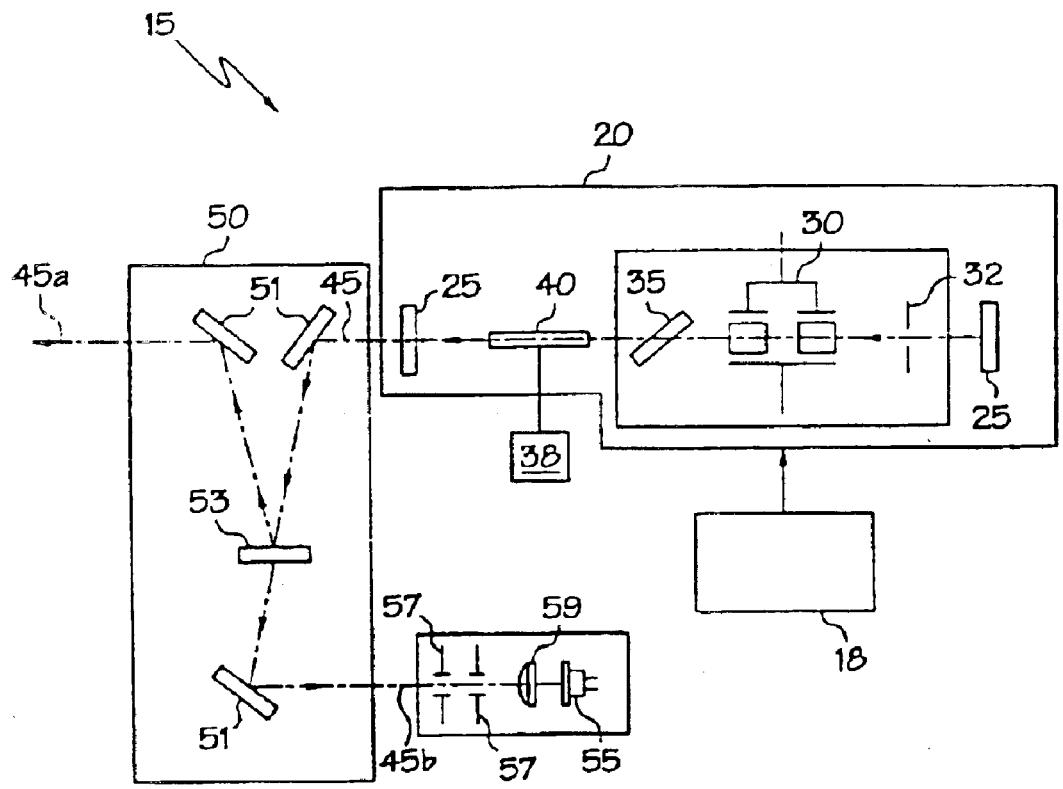
FIG. 2 is a schematic depiction of a laser system for use in the inventive method.

A number of different laser systems may be used in the practice of the inventive method. One such laser system is shown schematically at 15 in FIG. 2. Laser system 15 comprises a resonator cavity 20 which is provided with a gain medium therein. A number of different gain media may be used in the laser. Desirably, the gain medium will be chosen to produce a beam in a wavelength range of 1030 nm to 2000 nm and more desirably, 1030 nm to 1070 nm. This may be achieved using, for example, a $Yb^{3+}$, $Er^{3+}$, or $Ho^{3+}$ laser. Mirrors 25 are located at either end of the resonator. Resonator cavity 20 further comprises a modulator 30 in communication with pulse generator 18, an aperture 32 and a polarizer 35. An additional KTP crystal 40 for second harmonic generation is provided to transform a sample of the fundamental mode energy into visible radiation to facilitate alignment of the laser. The gain medium is pumped with a pump 38. Desirably, the pump will be pulsed. The pump may also be continuous wave (cw).

A Nd-Yag (Neodymium-Yttrium Aluminum Garnet) laser may also be used in the practice of the invention. In order to avoid losses due to birefringence of the Nd-Yag crystal, it may prove desirable to uniformly pump the Nd-Yag laser rod via diode pumping of the Nd-Yag laser rod. Losses due to birefringence may also be mitigated by varying the shape and/or the shape of the crystal, optionally in conjunction with the use of diode pumping of the crystal. For example, crystals of a shorter length may result in less birefringence than crystals of a longer length. By diode pumping, it may also be possible to achieve a smaller spot size Samples of the output laser beam 45 are provided using mirror arrangement 50 which splits output laser beam 45 into a main component 45a and a first sample component 45b. Mirror arrangement 50 includes mirrors 51 and beam splitter 53 and may be made using conventional optical elements. Sample component 45b is directed through apertures 57 and lens with attenuator 59 to photoelement 55 for monitoring the beam. Main component 45a is output toward the stent preform.

The operation of the laser may be further understood with reference to FIGS. 3a–d. When operated in a free lasing regime, during any given pump period 110, shown in FIG. 3a, a pulse of laser radiation 120 such as that shown in FIG. 3b will be emitted from the laser. The pulse is characterized by random oscillations 124 in the intensity of the beam.

Figure 3A:
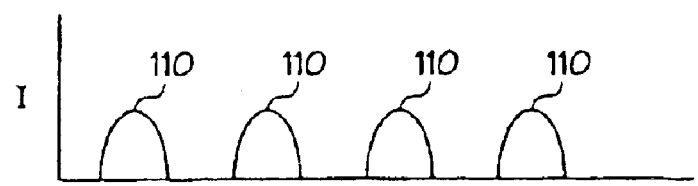
FIG. 3a depicts the output of a pump for pumping a laser.
Figure 3B:
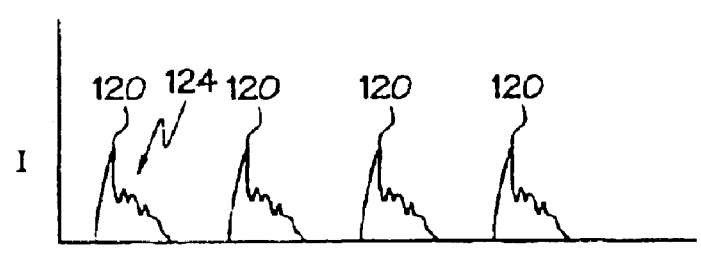
FIG. 3b depicts the output of a pumped free lasing laser.
Figure 3C:
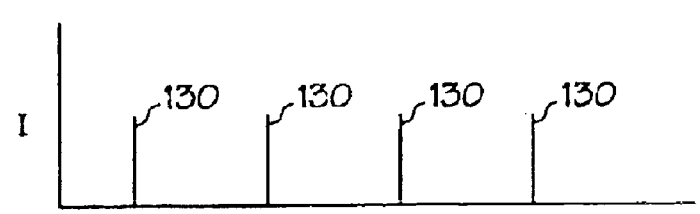
FIG. 3c depicts the output of a periodically pumped Q-switch laser.

When operated with a Q-switch, as shown in FIG. 3c, the laser will produce a single, high intensity beam 130. A Q-switch operates by maintaining the Q of the cavity low while a population inversion is created in the gain medium as a result of pumping. The low cavity Q prevents the laser from lasing. At a desired time, after a desired amount of energy is stored, the Q of the cavity is rapidly increased thereby facilitating stimulated emission of the gain medium. A large pulse of laser radiation is emitted. Unlike during free lasing, the Q-switched pulse decreases in intensity without random fluctuations.

Figure 3D:
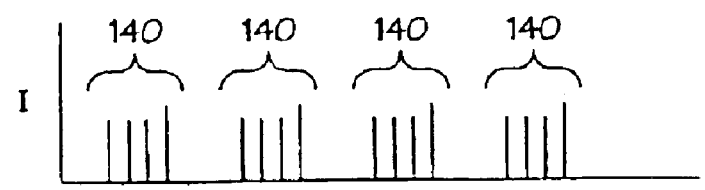
FIG. 3d depicts the output of a laser modulated in accordance with the inventive methods.
Figure 3E:
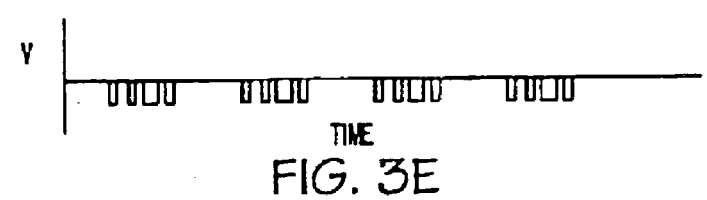
FIG. 3e depicts the time varying voltage supplied to a modulator in accordance with the invention.

In the inventive regime, as shown in FIG. 3d, multiple pulses of radiation 140 are produced during each pump period. Specifically, a periodic voltage is applied to the modulator. Desirably, the modulator will comprise a pockels cell. Other suitable electro-optical modulators as known in the art may also be used. The modulator is constructed and arranged such that on the application of a negative voltage thereto, the resonator cavity is closed. When zero voltage is applied to the modulator, the cavity is open, and the optical pulse can be switched out of the cavity as shown in FIG. 3e. By pulsing the voltage applied to the modulator, a series of laser pulses may be generated.

Desirably, the pulses will be up to 5 microseconds long. The exact pulse length depends on the choice of metal or other material being cut. For stainless steel, pulse lengths up to 5 microseconds in length in conjunction with an optical pump rate of 200–250 kHz are desirable. For Nitinol, pulse lengths up to 5 microseconds in length in conjunction with an optical pump rate of less than 200 kHz are desirable.

In applying the laser beam to the stent preform to cut a desired pattern therein, the stent preform may be moved relative to the laser beam or the laser beam may be moved relative to the stent preform. In the former case, the stent may be placed on a mandril and rotated and/or moved in longitudinal direction relative to the stent preform. In the latter case, the laser itself may be rotated about the stent preform and/or displaced longitudinally relative to the stent preform.

Figure 4:
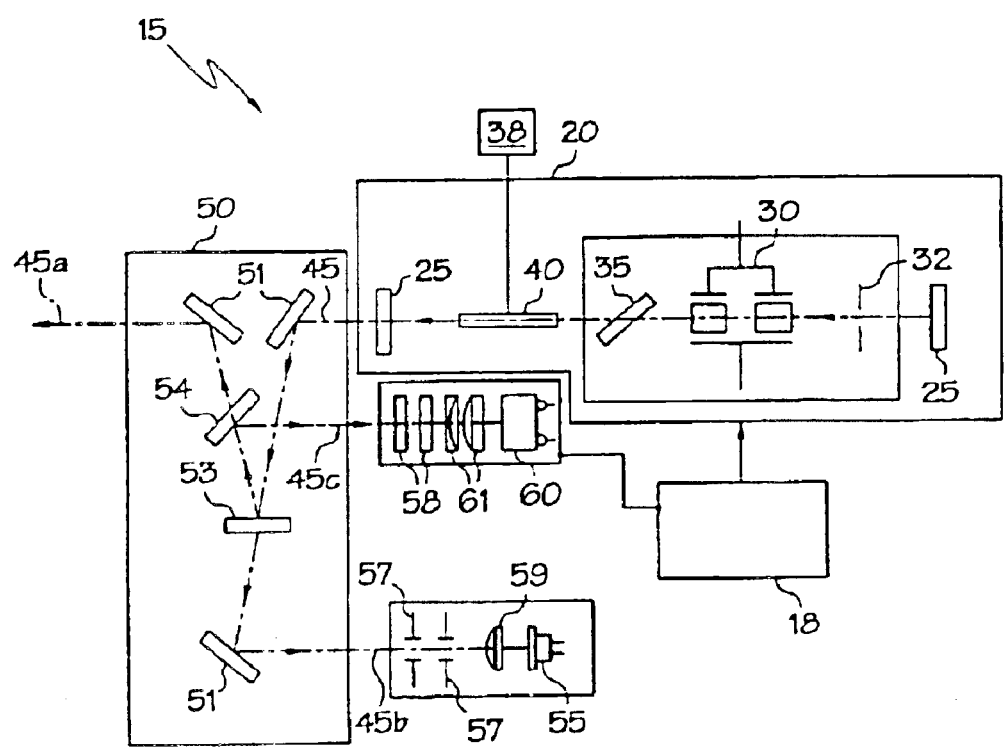
FIG. 4 is a schematic depiction of another embodiment of a laser system for use in the inventive method.

In another embodiment of the invention, a laser system such as that described above and shown in FIG. 2 may be modified to operate in a negative feedback mode. The laser system of FIG. 4 includes all of the elements of the laser system of FIG. 2 and further includes an additional beam splitter 54 which produces another sample component 45c of laser beam 45. Sample component 45c is directed through attenuators 58, lenses 61 and strong current photoelement 60 which is in electrical communication with pulse generator 18 and modulator 30. As the gain medium begins to lase, sample component 45c is converted via photo element 60 into an electrical signal which causes modulator 30 to prevent substantially all of the radiation in the cavity from exiting the cavity. In the meantime, with the absence of any radiation entering the photoelement and the absence of any voltage on the modulator, cavity 20 opens again, and a new pulse of laser radiation is emitted therefrom. The feedback loop is allowed to continue for a desired period of time thereby producing a series of laser pulses.

The above described negative feedback loop laser system may be used to treat a stent. A stent is provided along with a negative feedback loop laser system as described above. The pulse trains output by the laser may be characterized by an amplitude, a pulse width, an inner train separation time between subsequent pulses in a pulse train, and an inter train separation time between subsequent pulse trains. The pulses may be conditioned using an electro-optical modulator which forms a part of feedback loop and the amplitude, pulse width, inner train separation time and inter train separation time selected to polish, harden or engrave those portions of the stent impinged by the pulse trains.

As an example, a stent pattern was cut into a Nitinol tube using a pulse train generated as described above. Pulses of one to two nanoseconds in duration with a pulse repetition rate on the order of at least 250 kHz or more were used. An assist gas such as oxygen in conjunction with compressed nitrogen (for cooling) was used in the cutting process. Other suitable assist gases including Ar, He or mixtures of gasses may be used in place of or in addition to oxygen. Other inert gases may be substituted for the nitrogen gas as a coolant. Water may also be used to cool the stent. Following cutting of the tube, the kerf had a smooth and clean appearance. The heat affected zone adjacent to the cut appear narrower than the heat affected zone adjacent to cuts made using free lasing pulses. The dross and the slugs were of a deep black color and of a dense powder consistency which could be removed easily from the surface of the stent. The color and consistency differed from that which would result from cutting in a free lasing regime.

Without being bound by theory, it is believed that the relatively short, intense laser pulses produce an intense heating to high temperatures of a limited volume of metal thereby causing melting, evaporation and expulsion of metal from the surface impinged by the beam beyond that which results from the spikes associated with free lasing. Relatively small portions of overheated metal in the oxygen flow burns and precipitates as a powder on the metal surface resulting in a much finer structure of striations, if any, on the surface of the kerf. This in turn results in a reduction of microcracks with the attendant increase in mechanical durability of the struts of the stent. The energy density associated with the free lasing regime, in comparison, results in melting and recrystallization of metals in the melted metal bath with increased prevalence of striations, microcracks and a reduced durability.

Desirably, the pulses will be of no more than 2 microseconds in duration. More desirably, the pulses will be of no more than 1 microsecond in duration.

More generally, the invention is directed to a method of treating a workpiece comprising the steps of providing a workpiece and providing a laser system comprising an optical cavity for resonating laser radiation, an optical gain medium contained in the optical cavity, an optical pump for periodically pumping the optical gain medium, the laser system producing a radiation pulse for each pump period. Each radiation pulse is conditioned to produce a pulse train of ordered pulses of radiation, directed at desired portions of the workpiece and impinged onto desired portions of the workpiece. In certain embodiments, the pulses may be conditioned using an electro-optical modulator which forms a part of feedback loop and the pulse trains may be characterized by an amplitude, a pulse width, an inner train separation time between subsequent pulses in a pulse train, and an inter train separation time between subsequent pulse trains and the amplitude, pulse width, inner train separation time and inter train separation time are selected to perform a treatment selected from the group consisting of engraving, hardening, cutting and polishing.

In another embodiment, the invention is directed to a method of treating a stent comprising the steps of providing a stent, providing a laser system comprising an optical cavity for resonating laser radiation, an optical gain medium contained in the optical cavity and an optical pump for periodically pumping the optical gain medium. The laser system produces a radiation pulse for each pump period. Each radiation pulse is conditioned to produce a pulse train of ordered pulses of radiation. Each of the pulse trains is directed at desired portions of the stent and impinged onto desired portions of the stent. The pulse trains may be characterized by an amplitude, a pulse width, an inner train separation time between subsequent pulses in a pulse train, and an inter train separation time between subsequent pulse trains. In certain embodiments, the pulses may be conditioned using an electro-optical modulator which forms a part of feedback loop and the amplitude, pulse width, inner train separation time and inter train separation time selected to polish, harden or engrave those portions of the stent impinged by the pulse trains.

In another embodiment, the invention is directed to a method of treating a workpiece comprising the steps of providing a workpiece and providing a laser system comprising an optical cavity for resonating laser radiation, an optical gain medium contained in the optical cavity, an optical pump for periodically pumping the optical gain medium, the laser system producing a radiation pulse for each pump period. Each radiation pulse is conditioned to produce a pulse train of ordered pulses of radiation, directed at desired portions of the workpiece and impinged onto desired portions of the workpiece. In certain embodiments, the pulses may be conditioned using an electro-optical modulator which forms a part of feedback loop and the pulse trains may be characterized by an amplitude, a pulse width, an inner train separation time between subsequent pulses in a pulse train, and an inter train separation time between subsequent pulse trains and the amplitude, pulse width, inner train separation time and inter train separation time are selected to perform a treatment selected from the group consisting of engraving, hardening, cutting and polishing.

The invention also contemplates other embodiments in which laser pulses are conditioned by suppressing desired portions of the pulse and suitably conditioning the remainder of the pulse.

Figure 6:
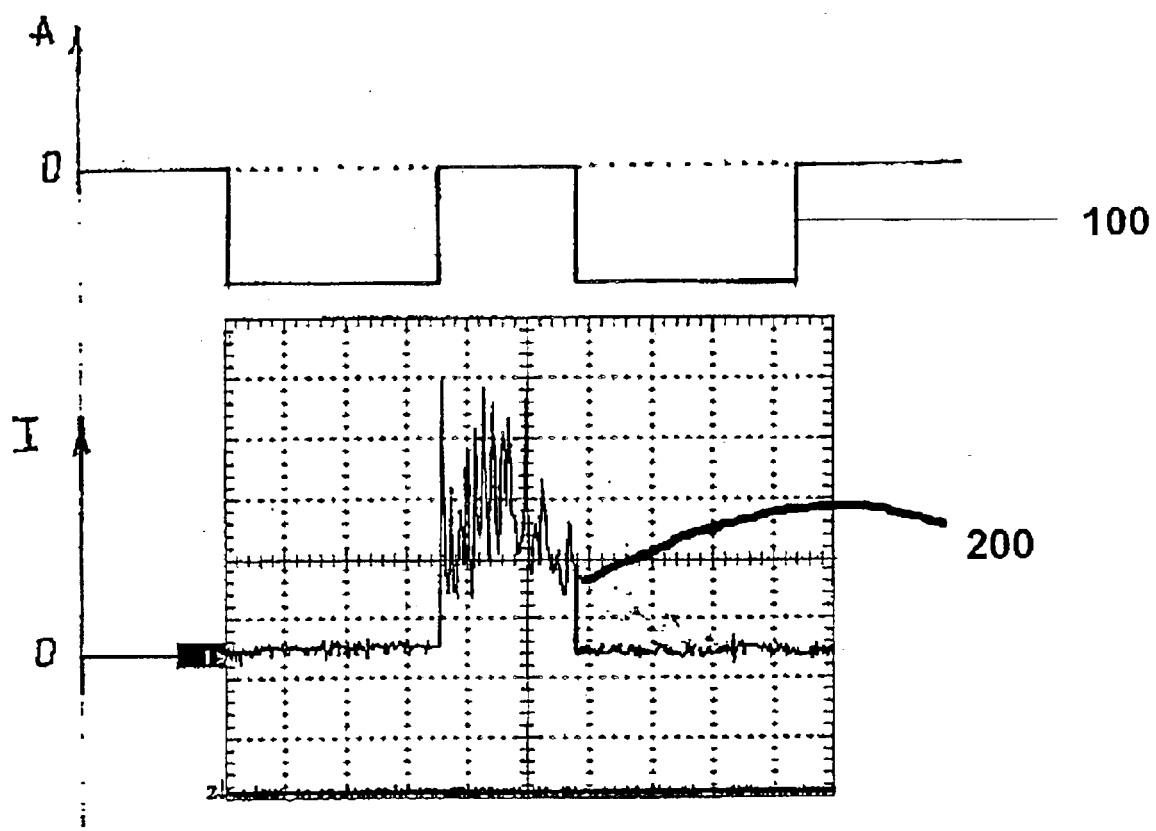
FIG. 6 depicts free lasing radiation that has been conditioned.

To that end, it is within the scope of the invention to suppress either the leading edge and/or the trailing edge of a laser pulse and optionally conditioning the remainder of the pulse and using the resulting radiation to cut a medical device such as a stent. For example, a laser pulse may be generated and an electrooptical modulator used to suppress the leading edge of the pulse, denoted by A in FIG. 1 as well as the trailing edge of the pulse, labeled by C in FIG. 1. FIG. 6 shows a suppressing pulse (curve 100) and the resulting pulse shape (curve 200) plotted as a function of time. A plurality of such pulses may be generated and directed at a workpiece for manufacturing a medical device. Each pulse may also be further conditioned using the above-disclosed techniques to create a pulse train from each pulse. Using the apparatus discussed above, during free lasing, a periodic voltage may applied to a modulator, such as, for example, a pockels cell. The modulator is constructed and arranged such that on the application of a negative voltage thereto, the resonator cavity is closed. When zero voltage is applied to the modulator, the cavity is open, and the optical pulse can be switched out of the cavity as shown. By pulsing the voltage applied to the modulator, a series of laser pulses may be generated from the free lasing pulse.

Figure 7:
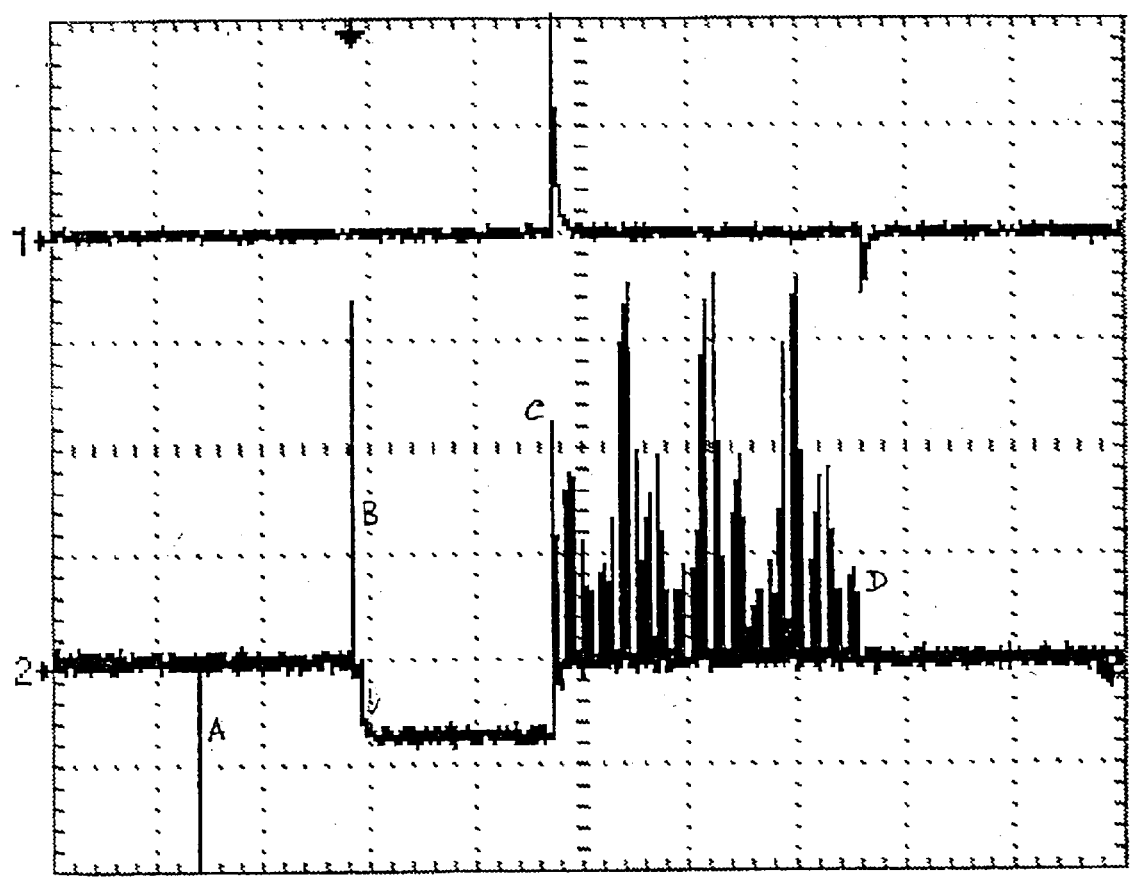
FIG. 7 illustrates a series of pulse trains generated by modulating a free-lasing pulse.

FIG. 7 illustrates a series of pulse trains generated by modulating a free-lasing pulse. As shown in FIG. 7, free lasing is suppressed via the use of a suppressing pulse between times A and B. At time B, modulation of the laser pulse is commenced resulting in a pulse train. As shown at curve 200 in FIG. 7, a series of pulse trains is produced. The generator pulses are shown at curve 100. FIG. 7 shows the intensity of the pulses as a function of time.

Figure 8:
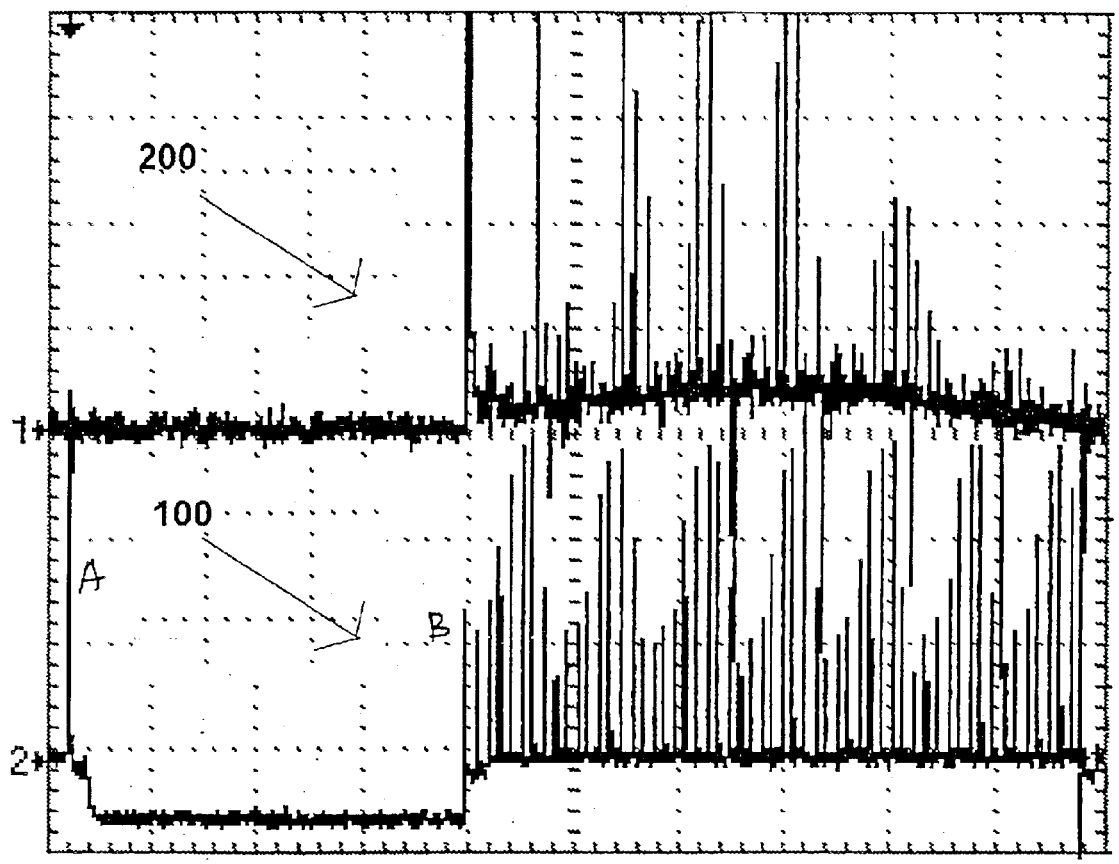
FIG. 8 illustrates a series of pulse trains generated by modulating a free-lasing pulse.

FIG. 8 also illustrates a series of pulse trains generated by modulating a free-lasing pulse similar to FIG. 7. As in FIG. 8, the generator pulses are shown in curve 100 and the series of pulse trains is shown at curve 200. FIG. 8 differs from FIG. 7 in that a longer optical pump pulse is being used.

Without being bound by theory, it is believed to be desirable, when laser cutting a metal workpiece, to bring the region to be cut to its melting point as quickly as possible without heating adjacent regions. Where the region to be cut is heated to less than its melting point for excessive periods of time, undesirable heat conduction into adjacent regions may result. In the case of Nitinol workpieces, this heating can result in regions around the area to be cut having alterations in their shape memory properties. It also may result in high stress areas and crack initiation points. Elimination of the leading edge and trailing edges of the laser pulse, which are not believed to provide sufficient energy to melt the metal, would reduce the extent of undesirable heat conduction and the resulting damage that it may cause.

More generally, the invention in one embodiment is directed to a method of processing a stent preform comprising the steps of providing a stent preform, providing a laser system which produces a radiation pulse for each pump period. The laser system comprises a) a resonator cavity for resonating laser radiation b) a gain medium contained in the resonator cavity and c) a pump for periodically pumping the gain medium. The method further comprises the steps of conditioning the radiation pulse by suppressing a portion of, but not the entirety of the radiation pulse to produce conditioned radiation, outputting the conditioned radiation in the form of a laser beam, directing the laser beam at the stent preform and impinging the laser beam onto the stent preform to cut a desired pattern in the stent preform.

Typically, the stent preform will be a tube and desirably, a tube made of Nitinol or stainless steel. The stent preform may also be a sheet of material, in which case the method further comprises the step of forming the sheet into a tube subsequent to the impinging step.

Optionally, only the beginning of the pulse or a portion thereof is suppressed. It is also within the scope of the invention for only the end of the pulse or a portion thereof to be suppressed or for both the beginning and the end of the pulse to be suppressed or portions thereof. The beginning of the pulse refers to that portion of the pulse, from the start of the pulse, which is capable of heating the substrate to be treated (i.e. the preform) but not of melting the substrate. The end of the pulse refers to that portion of the pulse, which, once melting has occurred, is capable of heating the substrate to be treated (i.e. the preform) but not of melting the substrate.

The conditioning step may further comprise conditioning each radiation pulse to produce a pulse train of ordered pulses of radiation for each radiation pulse as disclosed above in this disclosure.

The invention is also directed to a method of processing a medical device preform comprising the steps of providing a medical device preform, providing a laser system comprising a resonator cavity for resonating laser radiation, a gain medium contained in the resonator cavity and a pump for periodically pumping the gain medium where the laser system producing a radiation pulse for each pump period, conditioning the radiation pulse by suppressing a portion of, but not the entirety of the radiation pulse to produce conditioned radiation, outputting the conditioned radiation in the form of a laser beam, directing the laser beam at the medical device preform, and impinging the laser beam onto the medical device preform to modify the surface of the medical device preform.

Typically, the medical device preform will be a tube and desirably, a tube made of Nitinol or stainless steel. The medical device preform may also be a sheet of material, in which case the method further comprises the step of forming the sheet into a tube subsequent to the impinging step.

Optionally, only the beginning of the pulse or a portion thereof is suppressed. It is also within the scope of the invention for only the end of the pulse or a portion thereof to be suppressed or for both the beginning and the end of the pulse to be suppressed or portions thereof. The beginning of the pulse refers to that portion of the pulse, from the start of the pulse, which is capable of heating the substrate to be treated (i.e. the preform) but not of melting the substrate. The end of the pulse refers to that portion of the pulse, which, once melting has occurred, is capable of heating the substrate to be treated (i.e. the preform) but not of melting the substrate. Desirably, during the impinging step, a desired pattern is cut into the medical device preform.

The conditioning step may further comprise conditioning each radiation pulse to produce a pulse train of ordered pulses of radiation for each radiation pulse as disclosed above in this disclosure.

The methods disclosed herein may be used to cut any pattern into a stent preform or stent. Examples of stent patters are shown in WO 9626689 and U.S. Pat. No. 5,972,018.

Figure 5:
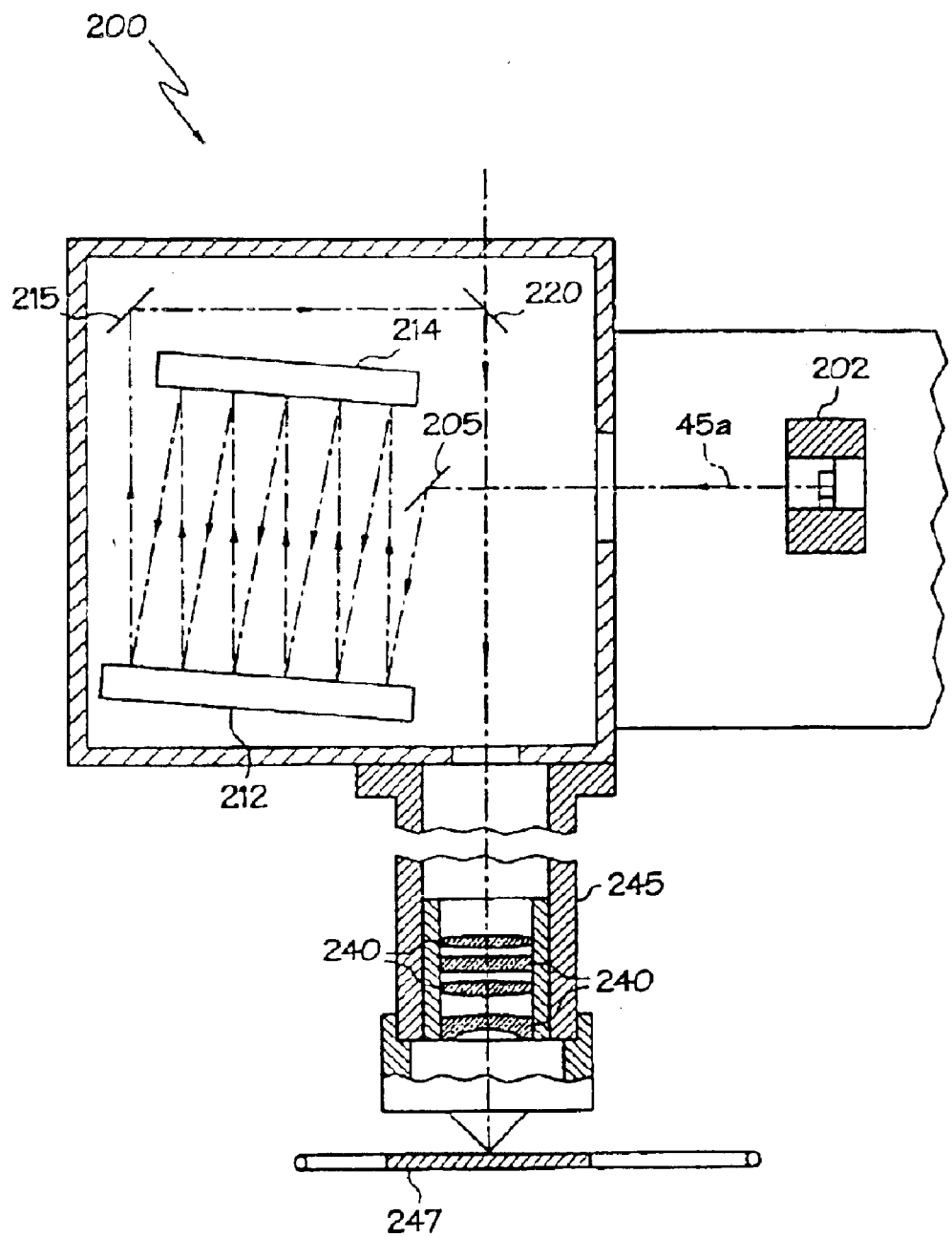
FIG. 5 depicts an inventive image processing head.

The invention is also directed to an image processing head, shown generally at 200 in FIG. 5. Head 200 includes a mask 202 first mirror 205, an optical path expander 210, a second mirror 215 and a third mirror 220. Beam 45a generated by a laser (not shown) enters head 200 and is redirected by mirror 205 into optical path expander 210. Optical path expander consists of two mirrors 212 and 214. Beam 45a bounces between mirrors 210 and 215 until it exits optical path expander 210 and is redirected out of the head by mirrors 215 and 220. Mirrors 205, 215 and 220 are desirably high reflectance mirrors. Similarly, mirrors 212 and 214 are also desirably high reflectance mirrors. The configuration and number of reflecting mirrors may be changed depending on the geometry of the housing. Beam 45a may be focused with a variety of lenses 240 in nozzle 245 prior to exiting the head and impinging on workpiece 247. Any suitable nozzle design may be used. The inventive image processing head may be used in any of the above embodiments of the invention. It has been found that using the inventive processing head, the optimal focus position was much less sensitive to both the aperture and focusing lens position.

Any of the inventive processes disclosed above may be used as a stand alone process or may be used in conjunction with other laser cutting processes. For example, the inventive processes may be used in conjunction with a cooling process in which a coolant such as a water-oil mixture is pumped through the workpiece as described in U.S. Pat. No. 5,073,694. Other coolants can include gas flows.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 7 may be taken as alternatively dependent from any of claims 2–6; claim 8 may be taken as alternatively dependent on any of claims 2–7; etc.).

What is claimed is:

1. A method of processing a stent preform comprising the steps of:
   providing a stent preform;
   providing a laser system comprising:
   a) a resonator cavity for resonating laser radiation
   b) a gain medium contained in the resonator cavity
   c) a pump for periodically pumping the gain medium, the laser system producing a radiation pulse for each pump period;
   d) conditioning the radiation pulse by suppressing a portion of, but not the entirety of the radiation pulse to produce conditioned radiation;
   e) outputting the conditioned radiation in the form of a laser beam
   f) directing the laser beam at the stent preform; and
   g) impinging the laser beam onto the stent preform to cut a desired pattern in the stent preform.

2. The method of claim 1 wherein the stent preform is a tube.

3. The method of claim 2 wherein the tube is made of Nitinol.

4. The method of claim 2 wherein the tube is made of at least one polymeric material.

5. The method of claim 1 wherein the stent preform is a sheet of material, the method further comprising the step of forming the sheet into a tube subsequent to the impinging step.

6. The method of claim 2 wherein the tube is made of stainless steel.

7. The method of claim 1 wherein only the beginning of the pulse is suppressed.

8. The method of claim 1 wherein only the beginning of the pulse and the end of the pulse are suppressed, a portion of the pulse between the beginning and the end not being suppressed.

9. The method of claim 1 wherein only the end of the pulse is suppressed.

10. The method of claim 9 wherein the laser beam is entrained in a column of water prior to being impinged against the stent perform.

11. The method of claim 1 wherein the conditioning step further comprises conditioning each radiation pulse to produce a pulse train of ordered pulses of radiation for each radiation pulse.

12. The method of claim 11 wherein the stent preform is formed of Nitinol.

13. The method of claim 1 wherein during the impinging step the stent preform is moved relative to the laser beam.

14. The method of claim 11 wherein during the impinging step the stent preform is moved relative to the laser beam.

15. A method of processing a medical device preform comprising the steps of:
   providing a medical device preform;
   providing a laser system comprising:
   a) a resonator cavity for resonating laser radiation
   b) a gain medium contained in the resonator cavity
   c) a pump for periodically pumping the gain medium, the laser system producing a radiation pulse for each pump period;
   d) conditioning the radiation pulse by suppressing a portion of, but not the entirety of the radiation pulse to produce conditioned radiation;
   e) outputting the conditioned radiation in the form of a laser beam
   f) directing the laser beam at the medical device preform; and
   g) impinging the laser beam onto the medical device preform to modify the surface of the medical device preform.

16. The method of claim 15 wherein the medical device preform is a stent preform.

17. The method of claim 16 wherein the stent preform is tubular.

18. The method of claim 17 wherein during the impinging step, a desired pattern is cut into the stent preform.

19. The method of claim 15 wherein only the beginning of the pulse is suppressed.

20. The method of claim 15 wherein only the beginning of the pulse and the end of the pulse are suppressed, a portion of the pulse between the beginning and the end not being suppressed.

21. The method of claim 15 wherein only the end of the pulse is suppressed.

22. The method of claim 15 wherein the conditioning step further comprises conditioning each radiation pulse to produce a pulse train of ordered pulses of radiation for each radiation pulse.

23. The method of claim 18 wherein the conditioning step further comprises conditioning each radiation pulse to produce a pulse train of ordered pulses of radiation for each radiation pulse.

* * * * *

UNITED STATES PATENT AND TRADEMARK OFFICE
CERTIFICATE OF CORRECTION

PATENT NO. : 6,867,389 B2  
DATED : March 15, 2005  
INVENTOR(S) : Vitaly Shapovalov et al.

Page 1 of 1

It is certified that error appears in the above-identified patent and that said Letters Patent is hereby corrected as shown below:

<u>Column 8,</u>
Line 38, after "may" add -- be --.

<u>Column 9,</u>
Line 49, after "system." change "producing" to -- produces --.

<u>Column 10,</u>
Line 14, change first word "patters" to -- patterns --.

Signed and Sealed this

Fourth Day of April, 2006

JON W. DUDAS
*Director of the United States Patent and Trademark Office*